United States Patent [19]

Razi

[11] Patent Number: 4,559,041
[45] Date of Patent: Dec. 17, 1985

[54] CANNULA INTRODUCERS

[76] Inventor: M. Dean Razi, 5800-49th St. N., St. Petersburg, Fla. 33709

[21] Appl. No.: 624,298

[22] Filed: Jun. 25, 1984

[51] Int. Cl.⁴ ............................................... A61M 5/00
[52] U.S. Cl. .................................... 604/157; 604/164; 128/305
[58] Field of Search ............... 604/157, 156, 164, 165, 604/161, 117; 128/305

[56] References Cited

U.S. PATENT DOCUMENTS

| | | | |
|---|---|---|---|
| 3,538,916 | 11/1970 | Wiles et al. | 604/117 X |
| 3,762,416 | 10/1973 | Moss et al. | 128/305 |
| 3,809,095 | 5/1974 | Cimber | 604/157 |
| 4,016,879 | 4/1977 | Mellor | 604/164 X |
| 4,137,920 | 2/1979 | Bonnett | 128/305 X |

Primary Examiner—Stephen C. Pellegrino
Attorney, Agent, or Firm—Ronald E. Smith; Harold D. Shall

[57] ABSTRACT

A cannula introducer device for providing a cut in a blood vessel wall and inserting a cannula into such cut. The device includes a rod housing carried by a pistol-shaped handle. Telescoped within the rod housing is a blade rod terminating at its distal end in a knife blade and extending from the proximal end of the rod housing to be secured to a reverse hammer-cam follower which is biased in a direction to move the blade rod proximately into the rod housing. Surrounding the rod housing and releasably carried by the handle is a cannula, the distal end being substantially co-extensive with the rod housing. A first trigger in the handle engages the reverse hammer and upon proximal movement of the trigger moves the blade out of the distal end of the rod housing and cannula where the operator can use the blade to cut an opening in the blood vessel. A spring loaded stop engages the trigger at its blade extended position. Further proximal movement of the trigger overcomes the stop and allows the reverse hammer to be biased to move the blade rod proximally into the confines of the rod housing. The entire device is then advanced distally to insert the distal end of the cannula in the cut in the vessel wall, and the cannula is then withdrawn from the handle and supporting blade housing. In a second embodiment, a second trigger is mounted on the handle and is spring loaded so that its upper end moves proximally. A rod pivotally secured to the upper end of the trigger extends distally into a notch at the proximal end of the cannula. Upon activation of the second trigger the rod pushes the cannula in a distal direction relative to the handle.

13 Claims, 14 Drawing Figures

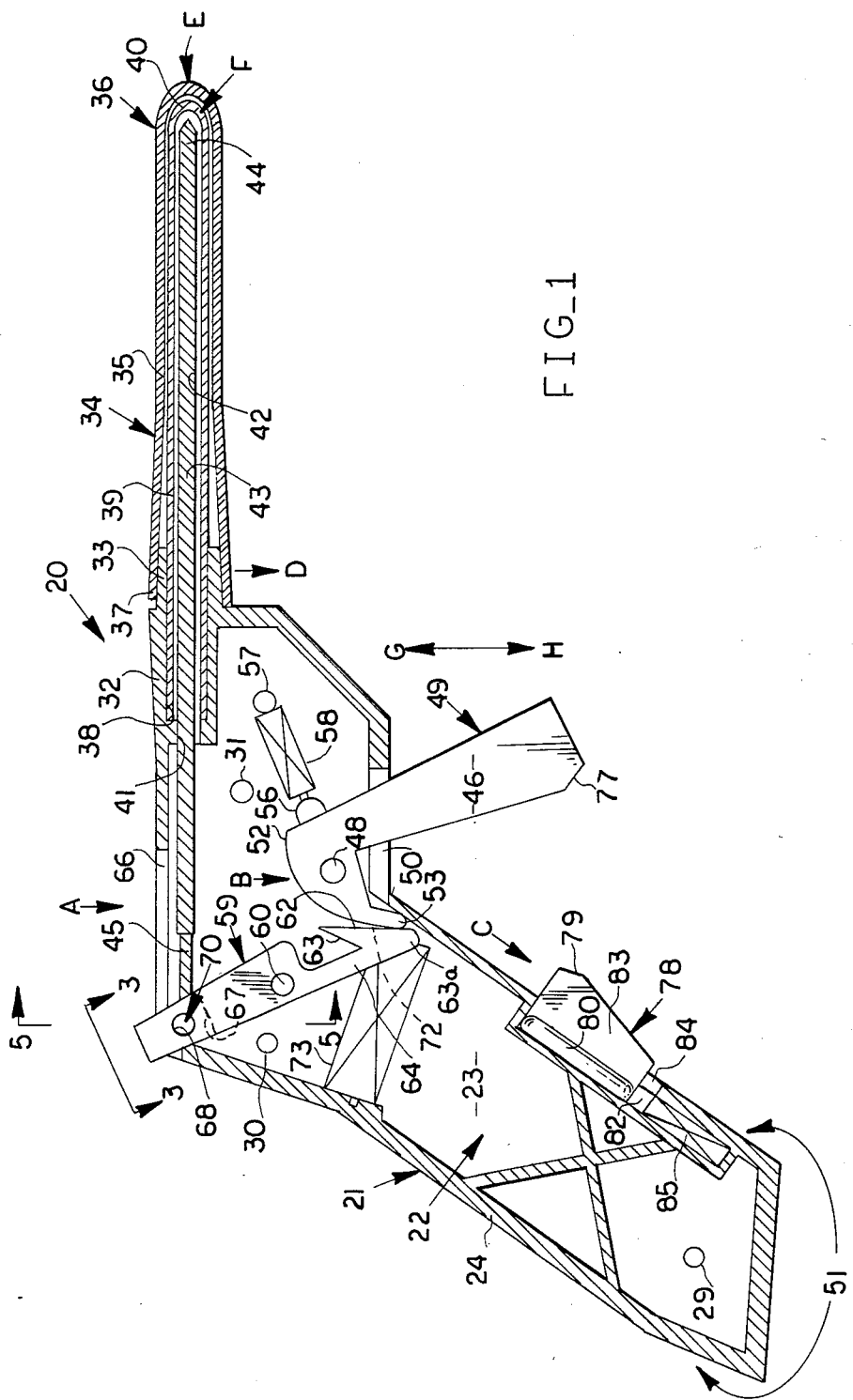
FIG_1

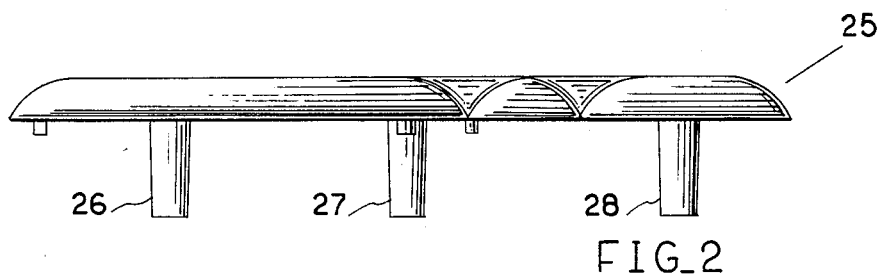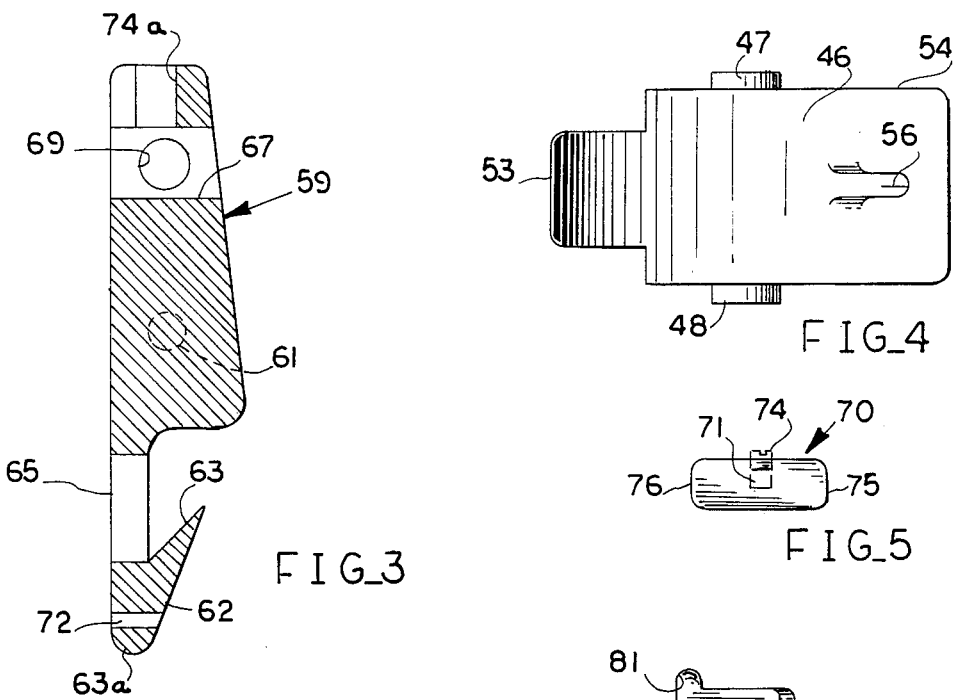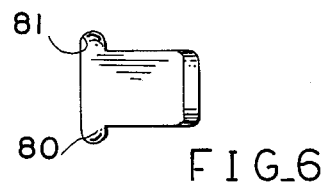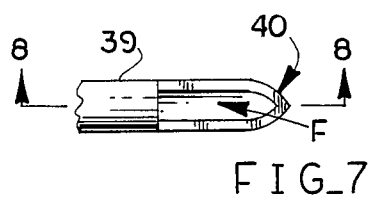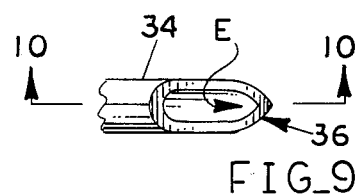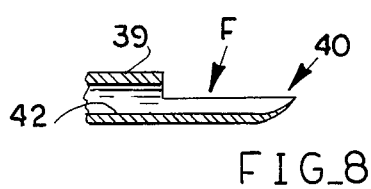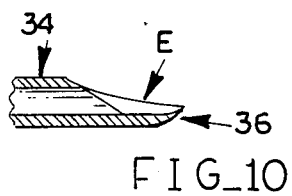

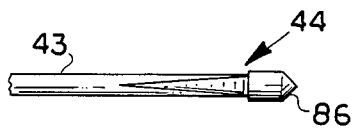
FIG_11
FIG_12
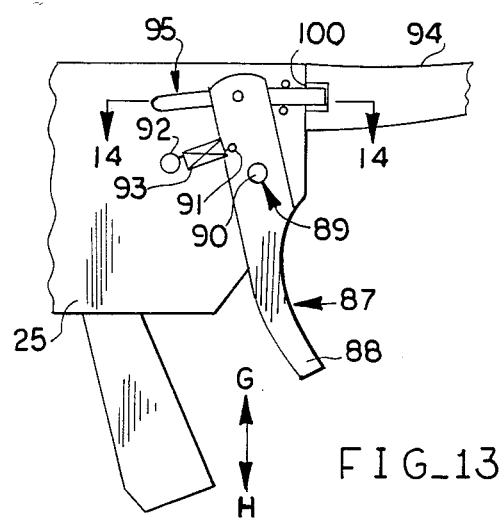
FIG_13
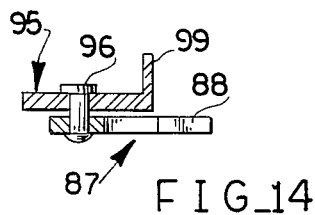
FIG_14

CANNULA INTRODUCERS

BACKGROUND OF THE INVENTION

1. Field of the Invention

This invention relates to an apparatus for making an opening through the wall of a blood vessel such as a vein or artery and for inserting into such opening so made a cannula.

2. Description of the Prior Art

Reference is made to my recently issued U.S. Pat. No. 4,411,653, entitled "Cannula Introducer" for a description of the prior art known at the time of filing that application. U.S. Pat. No. 3,762,416 entitled "Artery Entry Tool" provides for a tool to make an incision into an artery wall but does not have a trigger and release mechanism for the cutting blade that works in a manner to provide the desired ease of operation.

My above-mentioned U.S. Pat. No. 4,411,653, provides a rod housing, a blade-carrying rod within the housing, and a cannula carried by the housing for insertion into the blood vessel after making a slit therein by the blade. A blade-carrying rod is operated by a trigger to extend the blade to a cutting position wherein it extends from the end of the rod housing and cannula; however, after the cutting procedure, the surgeon or operator must release the trigger to withdraw the blade. The trigger is still operatively connected to the blade and if it is inadvertently moved, the blade can be extended to damage the cannula and when the cannula is removed from the blade, the blade can injure the patient, the operator, and those in the vicinity thereof.

SUMMARY OF THE INVENTION

The cannula introducer of the present invention provides a gun-like handle of the pistol type from which extends a rod housing; the rod housing having a proximal end mounted in the gun handle and a distal end extending axially from the handle. In order for the gun handle to not interfere with the adjacent patient's body, the gun handle is normally held in a plane which is substantially horizontal and not vertical as in the case of holding a conventional pistol. Accordingly, in the drawings accompanying this description, in the plan view of the invention, the gun handle looks like a side elevational view of a conventional pistol.

The rod housing is hollow and disposed telescopically therein is a rod or stylet terminating at its distal end in a blade with the proximal end of the stylet extending rearwardly of the rod housing and into the confines of the handle. The blade end of the rod in the cocked position of the introducer lies just within the distal end of the rod housing; while the proximal end of the blade carrying rod is secured in a cam follower member, which operates like a reverse pistol hammer, and which is mounted within the handle. A trigger is also mounted with a camming portion thereof within the handle to cooperate with the cam follower (reverse hammer) and a portion outside the handle where it can be operated by the operator. A first spring biases the trigger so that the finger-engaging portion thereof is disposed in a distal direction relative to the handle. A second spring biases the cam follower in a direction to move the blade rod in a proximal direction. The engagement between the trigger and the reverse hammer, when the trigger is in the cocked position, holds the knife end of the blade rod just within the confines of the blade housing. The finger-engaging portion of the trigger is movable distally and upon such movement cammingly operates the reverse hammer to extend the blade rod in a distal direction so that the blade end thereof projects beyond the end of the rod housing where it is in an operative cutting position. Signal means in the form of a spring-loaded stop are provided on the handle to engage the trigger at its position wherein the blade is extended the desired amount from the rod housing for the operator to cut an opening in the blood vessel. Further proximal movement of the trigger (after the desired cutting has been performed) overrides the signal means and allows the trigger to move to a position relative to the reverse hammer to allow the second spring means to bias the reverse hammer to its position wherein the blade rod is moved in a proximal direction so that its knife end lies within the rod housing and the reverse hammer is "fired" or uncocked. The signal means or spring-loaded stop tends to hold the trigger in its proximal position, which is an uncocked position.

A cannula has its proximal end slideably mounted on a mounting surface carried by the distal end of the handle and surrounds and is supported by the periphery of the rod housing; the distal end of the cannula is of a tapered beak shape and is substantially coextensive with, while projecting slightly beyond, the rod housing.

After the knife end of the blade rod has made its cut in the blood vessel and is then withdrawn into the rod housing by further proximal movement of the trigger, the entire apparatus can be advanced in the distal direction to insert the cannula into the opening which has been cut therefor by the blade. After such insertion, the cannula is held while the handle is moved in the proximal direction. This releases the slideable connection of the cannula to the mounting surface and withdraws the blade housing from the cannula. Since the cam follower is fired, or uncocked, at this time, inadvertent movement of the trigger during withdrawal of the cannula from the rod housing and subsequent to such withdrawal when the apparatus is being moved to a safe position, will not cause re-extension of the blade beyond the end of the rod housing and it will be confined in a safe location.

In a second embodiment of this invention, a second trigger is mounted on the handle distally relative to the first or blade actuating trigger. The second trigger has a distally extending rod pivotally secured thereto with the distal end of the rod inserted into a notch formed in the proximal end of the cannula. Upon actuation of the second trigger, the proximal end of the cannula is forced off the mounting surface of the handle.

It is contemplated that most of the components of this apparatus be made of plastic so that the apparatus can be inexpensive enough to be thrown away after a single use; such items as the blade rod, springs, and a few other portions are made of suitable metallic material. However, the device can be re-cocked, cleaned, sterilized and re-used if desired; its useful life being dependent upon the materials used and the desires of the operator.

BRIEF DESCRIPTION OF THE DRAWINGS

For a fuller understanding of the nature and objects of this invention, reference should be made to the following detailed description, taken in conjunction with the accompanying drawings in which:

FIG. 1 is a longitudinal sectional view of a cannula introducing device according to this invention with the trigger, the reverse hammer, and the spring-loaded stop shown in full lines; it being be understood that FIG. 1, if shown in full lines, would be a plan view of the device in its usual operative position;

FIG. 2 is a side elevational view of the cover plate for the handle portion of the device of FIG. 1 when viewed in the direction of arrow A in FIG. 1;

FIG. 3 is a cross sectional view of the reverse hammer taken along the line 3—3 in FIG. 1;

FIG. 4 is a side elevational view of the trigger of the device of FIG. 1 when viewed in the direction of the arrow B in FIG. 1;

FIG. 5 is a cross sectional view of the pivoted mounting pin taken along the line 5—5 in FIG. 1;

FIG. 6 is a view of the spring-loaded stop of the device of FIG. 1 when viewed in the direction of the arrow C in FIG. 1;

FIG. 7 is a plan view of the distal end portion of the rod housing;

FIG. 8 is a cross sectional view of the rod housing taken along the line 8—8 in FIG. 7;

FIG. 9 is a plan view of the distal end of a portion of the cannula;

FIG. 10 is a cross sectional view of the cannula taken along the line 10—10 in FIG. 9;

FIG. 11 is a plan view of the distal end of the stylet;

FIG. 12 is a side elevational view of the distal end of the stylet;

FIG. 13 is a plan view of the distal portion of a second embodiment of the handle of this invention along with the proximal portion of the cannula showing the second trigger; and FIG. 14 is a cross sectional view taken along the line 14—14 in FIG. 13 of the second trigger and a rod member extending distally therefrom to engage the cannula.

DETAILED DESCRIPTION OF THE PREFERRED EMBODIMENT

Referring to FIG. 1, a cannula introducer is shown generally at 20 and has a gun-like handle 21, which, as seen in FIG. 1, is a plan view (in section) in its normal operative position. The handle 21 has a cavity portion 22 enclosed on the bottom by a bottom wall 23, which wall is surrounded about substantially its entire periphery by an upstanding flange 24. The flange 24 extends upwardly for more than one-half of the thickness of the handle so that a cross sectional view as seen in FIG. 1 goes through the flange 24. As seen in FIG. 1, the left side of the indroducer 20 is the proximal direction in relation to the operator while the right side is the distal direction with respect to the operator and will hereinafter be so referred.

As seen in FIG. 2, a cover plate 25 is adapted to overlie and be secured on the handle 22, supported peripherally by the flange 24; the cover plate having three projections 26, 27 and 28 extending into the cavity portion 22 and adapted to be secured to the bottom wall 23 about the openings 29, 30 and 31, respectively, as by screws (not shown) extending conventionally from the underside of the handle (not shown) through the openings 29-31 in the bottom wall 23 and into the projections 26-28 respectively.

The flange 24 at the distal end of the handle 21 is enlarged internally to form a shoulder as shown at 32 and is enlarged externally of the flange 24 to form a truncated conical boss externally of the handle as shown at 33; the enlarged base of the conical boss is formed integral with the flange 24 of the handle and the distal end of the boss is the portion thereof which is truncated.

An elongated cannula 34 has a medial straight portion 35, a formed distal portion 36, to be more clearly hereinafter described, and a conically shaped proximal portion 37. The internal surface of the cannula's proximal portion 37 is a mating fit on the conical boss 33; by mating fit is meant it is a sliding interference fit which securely yet releasably holds the cannula on the conical boss. The handle 21 adjacent the conical boss 33 is thick enough and the position of the boss 33 is selected so that the cannula does not project beyond the handle.

A central bore 38 is formed in the boss 33, which bore extends inwardly from the outer end of the boss 33 and into the enlarged shoulder 32, but terminates slightly distally of the proximal end of the shoulder. Suitably secured in the bore 38, as by gluing, is a hollow rod housing 39 which is cylindrical for its entire length, except for the distal end 40 thereof as more fully described hereinafter. The rod housing 39 extends distally from the boss 33, and lies within and supports the cannula 34 in a sliding fit for its full length, except for the proximal conical portion 37 of the cannula which is spaced from the rod housing 39. To the left of the bore 38 in the boss 33 is a slightly smaller bore 41 which is approximately equal in size to the bore 42 in the rod housing 39.

Telescopically received within the bore 41 of the shoulder 32 and the bore 42 of the rod housing 39 is a blade rod or stylet 43 (which stylet except for its distal and proximal ends is cylindrical); the stylet 43 terminating at its distal end 44 in a cutting blade more fully described hereinafter. The cannula 34 is open at its distal end 36 as shown at E in FIGS. 1, 9 and 10 and the rod housing 39 is also open at its distal end as shown at F in FIGS. 1, 7 and 8. These openings allow the distal end 44 of the stylet 43 to project out of the rod housing and cannula during certain stages of operation of the device 20.

The stylet 43 extends proximally of the shoulder 32 to terminate at its proximal end in a square (in cross section) proximal projection 45.

For the purpose of clearly describing the first and second triggers, the reverse hammer and the spring-loaded stop, since FIG. 1 is a plan view and the handle 20 is at the distal end of the device, in FIGS. 1, 3 and 13, the direction indicated by the arrow G will be identified as the left and the direction indicated by the arrow H will be identified as the right.

A stylet operating or first trigger 46 is provided for actuating the stylet 43. As seen in FIG. 4, the trigger has a pair of pivot pins 48 and 47 extending respectively upwardly and downwardly therefrom. Referring to FIG. 1, the pivot pin 47 (which cannot be seen in this view) extends downwardly into and is pivotally mounted in a hole (not shown) in the bottom wall 23 of the handle 21, while the pin 48 extends upwardly and into and is pivotally mounted in a hole (not shown) in the handle cover plate 25. A finger engageable portion 49 of the trigger 46 extends to the right out of the handle 21 through a slot 50 formed in the right side flange 24 of the handle, which slot is located just distally of the graspable portion 51 of the handle 21.

As seen in FIG. 1, the left end 52 of the trigger 46 is disposed within the handle 21 and the distal end of the left end of the trigger has a curved cam shape shown at 53, which cam appears to look like a parrot's beak. As seen in FIG. 4, the curved cam is thinner in the up and down direction than the wider portions of the trigger 46, while the lower side 54 and upper side 55 of the trigger adjacent the pins 47 and 48 respectively are wider than the cam 53 and are bearing surfaces which slideably engage the lower wall 23 and the wall of the cover 25 to laterally support the trigger.

An eye 56 is formed in the distal side of the trigger 46 and proximally of the eye 56 and slightly to the left thereof, a post 57 is secured to and projects upwardly from the bottom wall 23 of the handle 21. A tension coil trigger return spring 58 has its distal end secured to the post 57 and its proximal end secured to the eye 56 and constantly biases the trigger 46 in a counterclockwise direction to the cocked position as seen in FIG. 1, so that the finger portion 49 of the trigger 46 is constantly biased distally.

A reverse hammer or cam follower 59 is disposed in the cavity portion 22 of the handle 21 distally and to the left of the trigger 46. More particularly, the hammer 59 is angularly elongated as sen in FIG. 1 and intermediate its ends is an upper pivot pin 60 seen in FIG. 1 and a lower pivot pin shown in phantom at 61 in FIG. 3; the pin 61 extending downwardly into and is pivotally mounted in a hole (not shown) in the bottom wall 23 of the handle 21, while the pin 60 extends upwardly and into and is pivotally mounted in a hole (not shown) in the handle cover plate 25. The upper and lower surfaces of the reverse hammer 59 slidingly engage the bottom wall 23 and the wall in the cover plate 25 to laterally stabilize the hammer 59.

As seen in the cocked position of FIG. 1, the lower distal surface 62 of the hammer 59 is a cam surface adapted to cooperate with the cam surface 53 of the trigger 46. More particularly, the cam surfaces 53 and 62 abut each other in the cocked position of FIG. 1. Just to the left of the cam surface 62 is a proximally extending slot 63 which extends inwardly of the hammer 59 adjacent the cam 62. As seen in FIG. 3, the slot 63 extends completely through the hammer 59, and is bounded by an upper surface 64 (as seen in FIG. 1) and a lower surface 65 (seen in FIG. 3), so that the cam end 62 of the cam follower 59 is connected to the remainder of the cam follower around the slot 63. The space between upper 64 and lower 65 surfaces as well as the right to left sides of the slot 63 is large enough to receive the distal end 53 of the trigger which has the curved cam shape like a parrot's beak. Adjacent the right end 63a of the hammer 59 is an opening 72 which receives the distal end of a coiled compression spring 73 compressed between the latter and the proximal flange 24 of the handle 21. The spring biases the hammer counterclockwise to a stylet withdrawal position.

The left end of the hammer 59 projects through a slot 66 formed in the flange 24, which is formed therein at the junction of the left and proximal portions of the wall; slot 66 extending distally sufficient to allow the hammer to rotate clockwise, as seen in FIG. 1, to its uncocked position.

Adjacent the left outer end of the hammer 59 is an axially extending slot 67 (clearly seen in FIG. 3) which slot receives the proximal end of the square proximal portion 45 of the stylet 43. The cam follower or reverse hammer 59 has aligned upper and lower openings 68 and 69 (opening 68 is seen in FIG. 1, while opening 69 is seen in FIG. 3), which openings pivotally receive a pivot pin 70 seen in FIGS. 1 and 5. As seen in FIG. 5, the pivot pin 70 has a square opening 71 therein which receives the left proximal end of the square proximal projection 46 on the stylet 43.

A set screw 74 is threaded into the pivot pin 70 from the left upper surface thereof to secure the stylet projection 45 therein. The upper and lower ends 75 and 76, respectively, of the pivot pin 70 slide upon the bottom wall 23 of the handle and the inner wall (not shown) of the cover plate 25. The set screw 74 may be loosened to adjust the axial position of the stylet 43 relative to the cannula 34 and the rod housing during pivotal movement of the hammer 59. The pivot pin 70 travels a slightly arcuate path, and the square proximal portion of the stylet 45 is sufficiently flexible to allow for this arcuate movement to take place without breaking of the stylet 43.

Upon the operator moving the finger portion 49 of the trigger 46 distally, it will engage a spring loaded stop 78 to inform the operator that this position has been reached. Concurrently with reaching the spring loaded stop, the right distal tip of the cam surface 53 on the trigger 46 will have reached a position just to the right of the slot 63 and the reverse hammer 59.

The spring loaded stop 78 provides a resistance against further counterclockwise rotation of the trigger 46 upon the latter's engagement therewith, so that the operator knows that the stylet is at the maximum distal position. The stop 78 has a tapered surface 79 on the distal left corner thereof which is cammingly engaged by the tapered surface 77 on the trigger 46. The stop 78, as seen in FIG. 6, has upper and lower shoulders 80 and 81 respectively, formed along the proximal edge thereof. These shoulders can be seen in FIG. 6, but only upper shoulder 80 can be seen in FIG. 1. Upper shoulder 80 slides in a slot (not shown) formed in the cover plate 25 while the lower shoulder 81 slides in a slot 82 formed in the handle 21 just proximally of the flange 24 at the distal side of the graspable portion 51 of the handle 21; the main body of the stop, distal of the shoulders 80 and 81, projecting distally through a slot 84 formed in the flange 24. The slot 82 in the handle 21 to the right side of the stop 78, and the registering slot (not shown) in the cover plate 25 extend to the right of the stop 78 and compressed between the lower end thereof and the bottom of the slot 82 is a coiled compression spring 85 which biases the stop 78 to the left.

Upon the trigger 46 being moved past the stop 78, the latter is biased to the right and the curved cam 53 on the trigger 46 enters the slot 63 in the hammer 59 and the spring 73 quickly fires the hammer 59; by firing is meant quickly rotates the same counterclockwise so that the stylet is in its withdrawn or proximal position. Since the cam 53 is in the slot 63 the trigger is no longer operative to move the stylet 43. Further, the spring loaded stop 78 will be biased to the left against the bottom of the trigger to help hold the trigger in the fired position.

To re-cock the reverse hammer 59, the left end thereof extending out of the slot 66 is forced distally by the operator while the cam 53 on the trigger 46 is withdrawn from the slot 63; the trigger 46 being moved counterclockwise to its position shown in FIG. 1, while the stop 78 is held to the right, to allow movement of the trigger. While the trigger is held in its counterclockwise position, the hammer is allowed to move counterclockwise so that the cam 53 on the trigger 46 once more engages the cam 62 on the reverse hammer or cam follower 59.

As seen in FIG. 1, the rod housing 39 is disposed within the cannula 34 and terminates just proximally of the end of the cannula 34. FIGS. 9 and 10 show that the distal end 36 of the cannula is formed with a lower beak-like configuration so that it may easily be moved into the opening formed in the blood vessel by advancing the entire cannula introducer 20 with the cannula thereon in the direction of the blood vessel. Once the distal end 36 of the cannula 34 is in the blood vessel the desired extent, the operator slips the proximal portion 37 of the cannula off of the conical boss 33 and withdraws the rod housing from within the cannula. The remaining manipulation and use of this cannula is well known in the art.

As seen in FIGS. 1, 7 and 8, the distal end 40 of the rod housing 39 is cut open at F like a lower beak; the curvature of the distal end being such that the housing can closely fit to the inner surface of the lower beak shaped end 36 of the cannula 34.

As seen in FIGS. 1, 11 and 12, the distal end 44 of the stylet 43 is formed with a suitable cutting end 86; it being understood that cutting ends of different configurations may be utilized. As seen in FIG. 12, the bottom of the cutting end 86 is formed on the center line off the stylet 43 so that it can move past the distal end 40 of the rod housing 39 and distal end 36 of the cannula 34 without interference or damage to the cannula or rod housing. When the distal end 44 of the stylet is in its cocked or withdrawn position, the cutting end 86 will lie within the confines of the distal end 40 of the rod housing 39 and thereby whether or not the cannula 34 is present, the cutting end 86 will not be in a position to cause inadvertent cutting.

Referring now to FIGS. 13 and 14, wherein a second embodiment is shown, and structures will have the same number as like structures of the embodiment of FIGS. 1-12, a second trigger or cannula separating means 87 is provided.

A trigger 87 has a rightwardly extending finger engaging portion 88 which, as seen in FIG. 13, projects to the right from a pivot pin 89 carried by the housing and pivotally mounting the trigger to the housing at a location intermediate the left and right ends of the trigger. The pivot pin 89 has an enlarged head 90 to prevent the trigger from coming off of the pin 89. To the left of the pivot pin 88, the trigger has an opening 91 substantially axially aligned with a post 92 carried by the cover plate 25. A coiled tension spring 93 has its opposed ends secured in the opening 91 and to the post 92 to bias the second trigger in a counterclockwise direction.

The second trigger 87 has a portion thereof extending to the left of the pivot pin 89 and the left end thereof extends somewhat past the center line of the modified cannula 94; the cannula 94 being mounted on a conical boss 33 (not seen in FIG. 13). A cannula ejector 95 is mounted to the left portion of the trigger 87. More particularly, as seen in FIG. 14, the ejector, when viewed from the left, is "L"-shaped in cross section. As seen in FIGS. 13 and 14, the ejector 95 extends distally from a pivot pin 96 which pivotally secures the ejector to the second trigger 87. A pair of spaced posts 97 and 98, the post 97 being to the left and the post 98 being to the right of the ejector 95 to substantially limit movement of the ejector in a proximal-distal direction; the fit not being so tight as to prevent some lateral rocking of the ejector as it moves proximally and distally since the pivotal connection at the trigger will move slightly arcuately.

The leg 99 of the "L"-shaped ejector 95 extends downwardly (downwardly as seen in FIG. 13) into a registering slot 100 formed in the proximal end of the cannula 94. To operate the second trigger 87; after the distal end of the cannula 94 has been introduced into the blood vessel, the finger engaging portion of the second trigger is moved proximally by the operator to force the cannula 94 off of the boss 33. This is accompanied by proximal movement of the handle 21 to withdraw the guide rod from within the cannula.

It will thus be seen that the objects set forth above, and those made apparent by the foregoing description, are efficiently attained, and since certain changes may be made in the above construction without departing from the scope of the invention, it is intended that all matters contained in the foregoing description, or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A cannular introducer device for providing a cut in a blood vessel wall and inserting a cannula into such cut comprising, a handle, a elongated cutting rod terminating at its distal end in a cutting blade means, said rod extending distally from said handle and being carried thereby for relative proximal and distal movement, a tubular rod housing carried by said handle and telescopically receiving at least the distal portion of said cutting rod, said cutting rod having a cutting position wherein the cutting blade means projects distally from said rod housing and a non-cutting position wherein said cutting blade means is shrouded by the distal end of said rod housing, an elongated hollow cannula, cannula supporting means on said handle for releasably supporting said cannula thereon with said cannula extending distally from said supporting means and said cannula telescopically receiving said rod housing and being supported by at least a portion of said tubular rod housing, trigger means carried by said housing and having a first end graspable by the operator of the device for actuating the same and a second end having operating means thereon, operated means carried by said handle and being connected to the proximal end of said cutting rod, said operated means having a first position wherein it maintains said cutting rod in its non-cutting position and having a second position wherein it maintains said cutting rod in its cutting position, first spring means biasing said operated means towards its first position, said operating means on said trigger means being operatively connected to said operated means, said trigger means having a first position wherein the operating means thereon maintains said operated means in the latter's first position, said trigger means being moveable to a second position wherein the operating means thereon moves said operated means to its second position and said trigger means having a third position wherein said operated means is allowed to be returned by said first spring means to its first position, and second spring means biasing said trigger means towards its first position.

2. A device according to claim 1 including a spring loaded stop means, said stop means being engaged by said trigger means when the latter is in its second position thereby indicating to the operator that said second position has been reached, said stop means being overridden by said trigger means when the operator moves said trigger means from its second to its third position.

3. A device according to claim 2 wherein said spring stop means resiliently engages said trigger means when the latter is, in its third position for resiliently holding the latter in such position.

4. A device according to claim 1, wherein said operating means on the second end of said trigger means is a first cam surface, said operated means is a cam follower having a second cam surface thereon, said first cam surface camming upon said second cam surface for moving said operated means between its first and second positions.

5. A device according to claim 4, wherein upon movement of said trigger means to its third position, said first cam surface moves from engagement with said second cam surface and said trigger means is not operative to move said operated means.

6. A device according to claim 1, including a second trigger means movably carried by said handle, said second trigger means including an abutment means engaging the proximal end of said cannula, and distal movement of said abutment means causing distal movement of said cannula relative to said handle.

7. A device according to claim 6, including resilient means normally biasing said abutment means proximally and manual operation of said second trigger means moves said abutment means distally.

8. A cannula introducer device for providing a cut in a blood vessel wall and inserting a cannula into such cut, comprising, a handle having a cavity therein, an elongated cutting rod having its proximal end disposed in said cavity and terminating at its distal end in a cutting blade, said rod extending distally from said handle and being carried thereby for relative proximal and distal movement, a tubular rod housing carried by said handle and telescopically receiving the portion of said cutting rod disposed distally of said handle, said cutting rod having a cutting position wherein said cutting blade projects distally from said rod housing and a non-cutting position wherein said cutting blade is shrouded by the distal end of said rod housing, an elongated cannula, cannula supporting means on said handle for releasably supporting said cannula thereon with said cannula extending distally from said supporting means and said cannula telescopically receiving said rod housing and being supported by at least a portion of said tubular rod housing, trigger means carried by said housing and having a first end graspable by the operator of the device contemporaneously with the operator's grasping the handle of the device for actuating said trigger means and said trigger means having a second end disposed in the cavity in said handle, said second end of said trigger means having a cam surface thereon, a reverse hammer pivotally mounted to said handle within the cavity therein, said hammer having a first end and second end with said first end being connected to the proximal end of said cutting rod within said cavity and said second end being a cam follower, said reverse hammer having a first position wherein it maintains said cutting rod in a non-cutting position and having a second position wherein it maintains said cutting rod in its cutting position, first spring means biasing said reverse hammer towards its first position, said cam surface of said trigger means being operatively engageable with said cam follower on said reverse hammer, said trigger means having a first position wherein said cam surface maintains said reverse hammer in said latter's first position, said trigger means being movable to a second position wherein said cam surface moves said reverse hammer to its second position and said trigger means having a third position wherein said cam surface does not engage said cam follower and said reverse hammer is allowed to be returned by said first spring means to its first position, and second spring means biasing said trigger means towards its first position.

9. A device according to claim 8 including a spring loaded stop means, said stop means being movably carried by said handle and being engaged by said trigger means when the latter is in its second position thereby indicating to the operator that said second position has been reached, and said stop means being resiliently overridden by said trigger means when the operator moves said trigger means from its second to its third position, said second position being more distal than said first position and said third position being more distal than said second position.

10. A device according to claim 9 wherein said spring stop means resiliently engages said trigger means when the latter is in its third position for resiliently holding the latter in such position.

11. A device according to claim 8 wherein upon movement of said trigger means to its third position said cam surface is not operative to cause movement of said reverse hammer.

12. A device according to claim 8 including a second trigger means movably carried by said handle, said second trigger means including an abutment means engaging the proximal end of said cannula, and distal movement of said abutment means causing distal movement of said cannula relative to said handle.

13. A device according to claim 12 including resilient means normally biasing said abutment means proximally and manual operation of said second trigger means moves said abutment means distally thereby causing distal movement of said cannula.

* * * * *